US00PP21268P2

(12) United States Plant Patent
Danziger

(10) Patent No.: US PP21,268 P2
(45) Date of Patent: Aug. 31, 2010

(54) ***CALIBRACHOA* SP. PLANT NAMED 'DANOA38'**

(50) Latin Name: ***Calibrachoa* sp.**
Varietal Denomination: DANOA38

(76) Inventor: Gabriel Danziger, PO Box 24 Moshav Mishmar Hashiva, Beit Dagan (IL) 50297

( * ) Notice: Subject to any disclaimer, the term of this patent is extended or adjusted under 35 U.S.C. 154(b) by 0 days.

(21) Appl. No.: 12/383,770

(22) Filed: Mar. 27, 2009

(51) Int. Cl.
*A01H 5/00* (2006.01)

(52) U.S. Cl. ..... Plt./413

(58) Field of Classification Search ..... Plt./413
See application file for complete search history.

*Primary Examiner*—June Hwu

(57) ABSTRACT

A new and distinct *Calibrachoa* cultivar named 'DANOA38' is disclosed, characterized by having bright pink flowers mounded plant habit, and large flowers. The new variety is a *Calibrachoa*, normally produced as an outdoor garden or container plant.

2 Drawing Sheets

Figure 1:
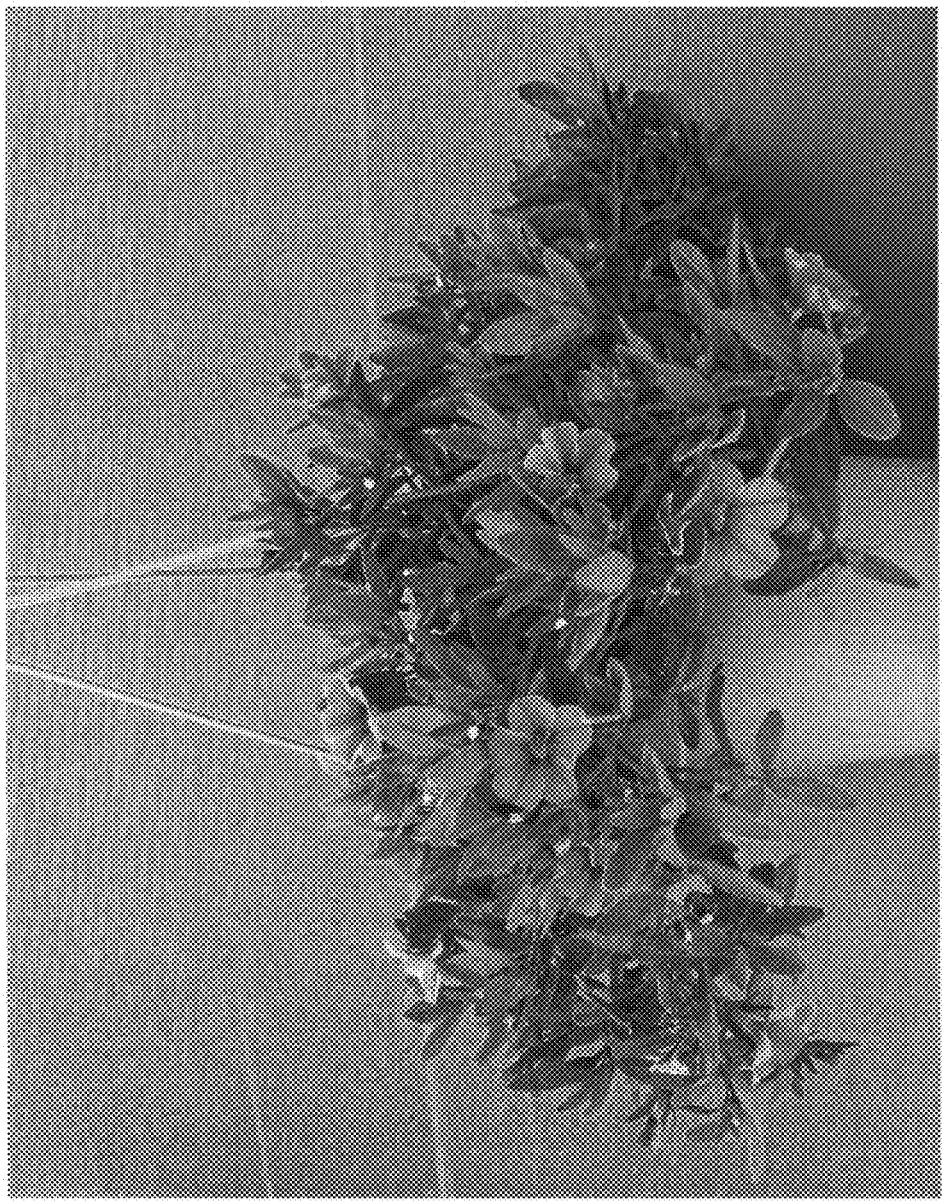

Latin name of the genus and species: *Calibrachoa* sp.
Variety denomination: 'DANOA38'.

BACKGROUND OF THE INVENTION

The new *Calibrachoa* cultivar is a product of a planned breeding program conducted by the inventor, Gabriel Danziger, in Moshav Mishmar Hashiva, Israel. The objective of the breeding program was to produce new varieties of *Calibrachoa* for commercial introduction. The seed parent is the unpatented, proprietary seedling variety referred to as *Calibrachoa* sp. 'CA-1295'. The pollen parent is unpatented, proprietary variety referred to as *Calibrachoa* sp. 'CA-793'. The crossing was performed during 2006.

The new variety was discovered in March 2007 by the inventor in a group of seedlings resulting from that crossing, in a commercial greenhouse in Moshav Mishmar Hashiva, Israel. Asexual reproduction of the new cultivar 'DANOA38' by vegetative cuttings was first performed at a commercial greenhouse in Moshav Mishmar Hashiva, Israel in March 2007. Subsequent propagation has shown that the unique features of this cultivar are stable and reproduced true to type on successive generations.

SUMMARY OF THE INVENTION

The cultivar 'DANOA38' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOA38' These characteristics in combination distinguish 'DANOA38' as a new and distinct *Calibrachoa* cultivar:

1. Bright pink color flower.
2. Large flowers.
3. Mounded plant habit.

PARENTAL COMPARISON

Plants of the new cultivar 'DANOA38' are similar to plants of the parent, *Calibrachoa* sp. 'CA-1295' in most horticultural characteristics, however, plants of the new cultivar 'DANOA38' have a much more free branching habit, darker pink flower color and a larger flower .

Plants of the new cultivar 'DANOA38' are similar to plants of the parent, *Calibrachoa* sp. 'CA-793' in most horticultural characteristics, however, plants of the new cultivar 'DANOA38' have a slightly more free branching habit, pink flower color, compared to white of the pollen parent and a larger flower than the pollen parent.

COMMERCIAL COMPARISON

Plants of the new cultivar 'DANOA38' can be compared to the commercial variety 'DANOA35' U.S. Plant Pat. No. 19,779. Plants of 'DANOA38' are similar to plants of 'DANOA35' in most horticultural characteristics, including plant habit and branching characteristics. However, plants of the new variety produce pink flowers whereas 'DANOA35' produces orange flowers with colored veins. Additionally, the new variety produces larger flowers than 'DANOA35'.

Plants of the new cultivar 'DANOA38' can also be compared to the commercial variety 'DANCALMIDBLU' U.S. Plant Pat. No. 18,123. Plants of 'DANOA38' are similar to plants of 'DANCALMIDBLU' in most horticultural characteristics, however, plants of the new variety produce pink flowers whereas 'DANCALMIDBLU' produces blue Additionally, the new variety produces larger flowers than 'DANCALMIDBLU'.

BRIEF DESCRIPTION OF THE PHOTOGRAPH

The accompanying photograph in FIG. 1 illustrates in full color a typical plant of 'DANOA38' grown in a greenhouse, in a 16 cm pot. Age of the plant photographed is approximately 8 weeks from a rooted cutting.

Figure 2:
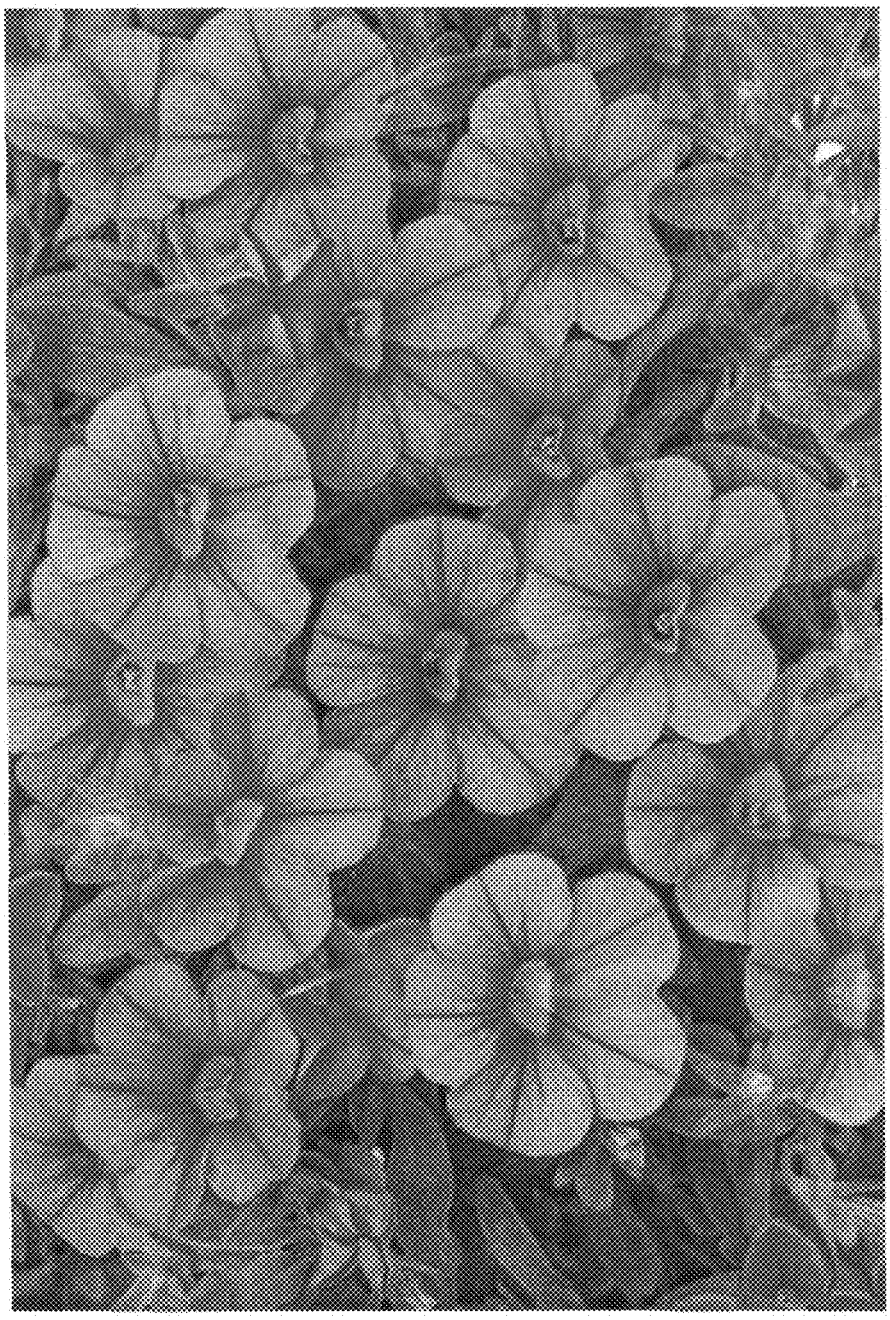

FIG. 2 illustrates in full color a close up of a typical bloom of 'DANOA38'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANOA38' plants grown outdoors, during the Fall in Moshav Mishmar Hashiva, Israel. The growing temperature ranged from 17° C. to 23° C. during the night and 20° C. to 35° C. during the day. Light conditions were bright, high sunlight conditions. Measurements and numerical values represent averages of typical plant types.

Botanical classification: *Calibrachoa* sp. 'DANOA38'.

PROPAGATION

Time to initiate roots: 10 to 14 days at approximately 18–35° C.

Root description: Fibrous.

PLANT

Growth habit: Trailing.
Pot size of plant described: Approximately 16 cm.
Height: To top of flowers: Approximately 7 cm.
Plant spread: Approximately 20 cm.
Growth rate: Moderate.
Branching characteristics: Free branching.
Length of primary lateral branches: Average 10 cm.
Diameter of lateral branches: Approximately 0.1 cm.
Quantity of primary lateral branches: 15.
Characteristics of primary lateral branches:
- *Form.*—Alternate.
- *Diameter.*—Approximately 0.2 cm.
- *Color.*—Near RHS Green 139A.
- *Texture.*—Pubescent.
- *Strength.*—Flexible.

Internodes length: Average 1–2.5 cm.

FOLIAGE

Leaf:
- *Arrangement.*—Opposite.
- *Quantity.*—Approximately 20 per branch.
- *Average Length.*—3 cm.
- *Average Width.*—1.3 cm.
- *Shape of blade.*—Oval.
- *Apex.*—Rounded.
- *Base.*—Acute.
- *Margin.*—Entire.
- *Texture of top surface.*—Glabrous.
- *Pubescence.*—Pubescent.
- *Aspect.*—90 degrees.
- *Color.*—Young foliage upper side: Near RHS Green 139A. Young foliage under side: Near RHS Green 139A. Mature foliage upper side: Near RHS Green 139A. Mature foliage under side: Near RHS Green 139A.

Venation:
- *Type.*—Pinnate.
- *Venation color upper side.*—Near RHS Green 139A.
- *Venation color under side.*—Near RHS Green 139A.

Petiole: No Petiole.

FLOWER

Natural flowering season: All year in Mediterranean climates.
Days to flowering from rooted cutting: Average 15–25 days.
Inflorescence and flower type and habit: Terminal, single, salverform, slightly downward nodding.
Rate of flower opening: 2 to 3 days from bud to fully opened flower.
Flower longevity on plant: 3–6 days.
Approximate quantity of flowers per plant: Approximately 20 open blooms, with approximately 70 buds.
Persistent or self-cleaning: Self-cleaning.

Bud:
- *Shape.*—Tubular.
- *Length.*—1.5 cm.
- *Diameter.*—0.5 cm.
- *Color.*—Near RHS Red-Purple N74C.

Flower size:
- *Diameter.*—Approximately 3.5 cm.
- *Flower tube length.*—Approximately 1.5 cm.
- *Flower tube diameter at distal end.*—Approximately 0.7 cm.
- *Flower tube diameter at proximal end.*—Approximately 0.4 cm.

Petals:
- *Length from throat.*—Approximately 1 cm.
- *Width.*—2 cm.
- *Quantity.*—5.
- *Texture.*—Smooth.
- *Apex.*—Blunt.
- *Margin.*—Entire.

Color:
- *When opening.*—Upper surface: Near RHS Red-Purple N74C. Lower surface: Near RHS Red-Purple N74D.
- *Fully opened.*—Upper surface: Near RHS Red-Purple N74C. Lower surface: Near RHS Red-Purple N74D. Flower throat (inside): Near RHS Yellow-Green 145C. Flower throat, veins: Near RHS Red-Purple 70A. Flower tube (outside): Near RHS Yellow-Green 145C. Flower tube, veins: Near RHS Red-Purple 70A.
- *Fading.*—Near RHS Red-Purple N74C.

Calyx/sepals:
- *Quantity per flower.*—5.
- *Shape.*—Elliptic.
- *Length.*—Approximately 1.5 cm.
- *Width.*—Approximately 0.3 cm.
- *Apex.*—Truncate.
- *Base.*—Cuneate.
- *Margin.*—Entire.
- *Texture.*—Lustrous.
- *Color.*—Upper surface: Near RHS Green 139A. Lower surface: Near RHS Green 139A.

Peduncle:
- *Length.*—Approximately 2.5 cm.
- *Diameter.*—Approximately 0.1 cm.
- *Color.*—Near RHS Green 139A.
- *Orientation.*—45 degree.

Fragrance: None.

REPRODUCTIVE ORGANS

Stamens:
- *Number.*—5.
- *Filament length.*—Approximately 0.6 cm.

Anthers:

*Length.*—Approximately 0.1 cm.

*Shape.*—Round.

*Color.*—Near RHS Yellow 11A.

*Pollen.*—Color: Near RHS Yellow 12A. Quantity: Profuse.

Pistil:

*Number.*—1.

*Length.*—Approximately 0.7 cm.

*Style.*—Length: Approximately 0.7 cm. Color: Near RHS Green 139C.

*Stigma.*—Shape: Round Color: Near RHS Green 139C. Ovary Color: Near RHS Green 139A.

OTHER CHARACTERISTICS

Seeds and fruits: Not observed.

Disease/pest resistance: Neither resistant nor susceptible to normal diseases and pests of *Calibrachoa*.

Temperature tolerance: 5–40° C.

What is claimed is:

1. A new and distinct cultivar of *Calibrachoa* plant named 'DANOA38' as herein illustrated and described.

* * * * *